US012564616B2

(12) United States Patent
Gersh

(10) Patent No.: US 12,564,616 B2
(45) Date of Patent: Mar. 3, 2026

(54) COMPOSITION FOR RESPIRATORY DISEASES

(71) Applicant: Sol Gersh, Bal Harbour, FL (US)

(72) Inventor: Sol Gersh, Bal Harbour, FL (US)

( * ) Notice: Subject to any disclaimer, the term of this patent is extended or adjusted under 35 U.S.C. 154(b) by 0 days.

(21) Appl. No.: 18/641,028

(22) Filed: Apr. 19, 2024

(65) Prior Publication Data

US 2024/0269222 A1     Aug. 15, 2024

Related U.S. Application Data

(63) Continuation-in-part of application No. 17/749,586, filed on May 20, 2022, now abandoned.

(51) Int. Cl.
*A61K 38/06*        (2006.01)
*A61K 36/534*       (2006.01)
*A61P 11/02*        (2006.01)

(52) U.S. Cl.
CPC ............ *A61K 38/06* (2013.01); *A61K 36/534* (2013.01); *A61P 11/02* (2018.01)

(58) Field of Classification Search
CPC .... A61K 38/06; A61K 36/534; A61K 9/0043; A61K 31/4174; A61K 31/4745; A61K 36/45; A61P 11/02
See application file for complete search history.

(56) References Cited

U.S. PATENT DOCUMENTS

| | | | | |
|---|---|---|---|---|
| 11,058,743 B2 * | 7/2021 | Arnold | ................. | A61K 9/0034 |
| 11,590,194 B2 * | 2/2023 | Carle | .................. | A61K 8/9789 |
| 12,150,971 B2 * | 11/2024 | Tuan | .................... | A61K 31/716 |
| 12,263,160 B2 * | 4/2025 | Jeffords | ............. | A61K 31/4468 |
| 2009/0281483 A1 * | 11/2009 | Baker | ................ | A61M 3/0212 |
| | | | | 604/35 |
| 2017/0326123 A1 * | 11/2017 | Shanley | .............. | A61K 36/736 |
| 2020/0352986 A1 * | 11/2020 | Green | .................. | A61K 31/375 |

FOREIGN PATENT DOCUMENTS

CN        111888350 A  * 11/2020

OTHER PUBLICATIONS

JP2014028777A, Feb. 13, 2014, Ohara Takaai, pp. 1-7 (Year: 2014).*

* cited by examiner

*Primary Examiner* — Aaron J Kosar
(74) *Attorney, Agent, or Firm* — Barry Choobin; Patent 360

(57)        ABSTRACT

A composition for the treatment and providing quick relief for respiratory diseases, such as Flu and Asthma. The composition includes reduced Glutathione; Mentha oil; Pyrroloquinoline quinone; Wintergreen oil; sodium nitrate; oxymetazoline hydrochloride; and excipients. The composition is administered through the nasal route.

5 Claims, No Drawings

COMPOSITION FOR RESPIRATORY DISEASES

CROSS-REFERENCE TO RELATED APPLICATIONS

This application is a continuation-in-part of a U.S. patent application Ser. No. 17/749,586 filed on May 20, 2022, which claims priority from a U.S. Provisional Patent Appl. No. 63/227,812 filed on Jul. 30, 2021, both of which are incorporated herein by reference in its entirety.

FIELD OF INVENTION

The present invention relates to a composition of respiratory diseases, and more particularly, the present invention relates to a composition for the treatment of respiratory diseases.

BACKGROUND

Several types of respiratory diseases affect humans, such as infections and allergies. Besides making a person sick, respiratory diseases can make people uncomfortable, irritated, and often restless. Viral infections are common respiratory diseases that affect many and often result in epidemics. There is no full-proof cure for viral infections available but only supportive treatments are provided. Similarly, for allergies such as chronic obstructive pulmonary disease (COPD) and Asthma, chiefly, supportive treatments are available. Because of the lack of a proper cure, people suffering from respiratory diseases/disorders often resort to alternative therapies, such as natural remedies for getting relief. Natural and herbal remedies are often considered safer than synthetic drugs and are widely adopted by people for a number of diseases. However, the known natural medicines for respiratory disorders are very mild in action and often prove unsatisfactory.

A need is therefore appreciated for a novel composition for the treatment and relief of respiratory diseases that is potent and safe.

SUMMARY OF THE INVENTION

The following presents a simplified summary of one or more embodiments of the present invention to provide a basic understanding of such embodiments. This summary is not an extensive overview of all contemplated embodiments and is intended to neither identify critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to a composition for the treatment and relief of respiratory disorders.

It is another object of the present invention that the composition is safe to use.

It is still another object of the present invention that the composition can provide quick relief.

It is a further object of the present invention that children and adults can use the composition.

It is yet another object of the present invention that the composition is natural and organic.

An additional object of the present invention is that significant healthcare costs can be prevented.

Still an additional object of the present invention is that the life span of people in general can be increased.

Yet an additional object of the present invention is that the life of millions can be saved every year.

In one aspect, disclosed is a composition that is based of natural resources and is edible and kosher.

In one aspect, disclosed is a composition that includes reduced glutathione (GSH), *Mentha* oil, pyrroloquinoline quinone (PQQ), wintergreen oil, sodium nitrate, and oxymetazoline hydrochloride. The composition can be used for the treatment and relief of respiratory diseases, such as viral infection, COPD, Asthma, and the like.

In one aspect, the disclosed composition includes reduced glutathione (GSH) 50-95%, *Mentha* oil 0.2-4%, pyrroloquinoline quinone (PQQ) 10-30%, wintergreen oil 0.2-4% sodium nitrate 0.1-0.5%, and oxymetazoline hydrochloride 0.01-0.10%. The rest can be water or any carrier medium.

DETAILED DESCRIPTION

The subject matter will now be described more fully hereinafter. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, reasonably broad scope for claimed or covered subject matter is intended. Among other things, for example, the subject matter may be embodied as compositions or methods of treatment. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is to describe particular embodiments only and is not intended to be limiting to embodiments of the invention. As used herein, the singular forms "a", "an", and "the" are intended to include the plural forms as well, unless the context indicates otherwise. It will be further understood that the terms "comprise", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely to illustrate the general principles of the invention since the scope of the invention will be best defined by the allowed claims of any resulting patent.

Unless otherwise indicated, all numbers expressing quantities of ingredients used in this disclosure are to be understood as being modified in all instances by the term "about." Accordingly, unless indicated to the contrary, the numerical parameters set forth in this disclosure are approximations that may vary depending upon the desired properties sought to be obtained by the present disclosure. At the very least, and not as an attempt to limit the application of the doctrine of equivalents to the scope of any claims, each numerical parameter should be construed in light of the number of significant digits and ordinary rounding approaches.

"Pharmaceutical composition" or "compositions" hereinafter refers to preparations that are in such a form as to permit the biological activity of the active agents to be unequivocally effective, and which contain no additional components which are toxic as administered to the patients.

"Subject" hereinafter refers to an individual and preferably a human who needs either relief and/or treatment. As used herein, a "subject" is the same as a "patient," and the terms can be used interchangeably.

'Treatment" hereinafter refers to medical treatment and includes both therapeutic and relief treatment depending on the context of use herein. "Treatment" includes reducing the virus load, preventing, or reducing complications, and symptomatic relief.

"Relief": refers to a decrease in intensity of symptoms associated with medical conditions.

The percentages mentioned herein are in volume percentages (vol %) if not mentioned otherwise. The vol % can be wt./vol % or vol/vol % depending on the context.

Disclosed is a composition for the treatment and relief of respiratory diseases, such as the diseases caused by viruses. The disclosed composition can provide quick relief in viral infections, such as Flu and Covid infections, and hastens recovery by promoting natural defense mechanisms of the body. The disclosed composition can also provide relief in allergies-related respiratory diseases, such as COPD and Asthma. The disclosed composition can be administered through the nasal route in subjects in need thereof for the treatment and providing relief for respiratory diseases.

In certain implementations, the disclosed composition can include reduced glutathione (GSH), *Mentha* oil, pyrroloquinoline quinone (PQQ), wintergreen oil, sodium nitrate, and oxymetazoline hydrochloride.

Glutathione is a tripeptide antioxidant that can protect underlying tissue from reactive oxygen species. Glutathione in the reduced form can be used.

*Mentha* oil can be obtained from the herb Mentha arvensis using suitable methods. Preferably, the *Mentha* oil can be of high purity, such as about 100% pure. Any known methods for producing *Mentha* oil from the herb are within the scope of the present invention.

Pyrroloquinoline quinone (PPQ), also known as methoxatin, is a redox cofactor and antioxidant.

Wintergreen oil is an essential oil obtained from herbs using suitable processes, such as steam distillation. Any methods for extracting wintergreen oil from herbs are within the scope of the present invention. Preferably, wintergreen oil of high purity can be used, such as about 100% pure wintergreen oil.

*Eucalyptus* oil is an essential oil that can be obtained from the herb *Eucalyptus radiata. Eucalyptus* oil obtained from *Eucalyptus globulus* is also within the scope of the present invention. *Eucalyptus* oil of high purity can be used, such as about 100% pure *Eucalyptus* oil. *Eucalyptus* oil can be obtained from herbs using suitable processes, such as steam distillation, and such processes are within the scope of the present invention.

Sodium nitrate is a chemical compound of formula $NaNO_3$, is a crystalline white powder.

Oxymetazoline hydrochloride is an alpha-1A adrenoceptor agonist that is chiefly used as a nasal decongestant.

In certain implementations, disclosed is a composition that includes reduced glutathione (GSH), *Mentha* oil, pyrroloquinoline quinone (PQQ), wintergreen oil, sodium nitrate, and oxymetazoline hydrochloride.

In certain implementations, the disclosed composition includes reduced glutathione (GSH) 50-95%, *Mentha* oil 0.2-4%, pyrroloquinoline quinone (PQQ) 10-30%, wintergreen oil 0.2-4%, sodium nitrate 0.1-0.5%, and oxymetazoline hydrochloride 0.01-0.10%.

In certain implementations, the disclosed composition includes reduced glutathione (GSH) 80.45%, *Mentha* oil 0.6%, pyrroloquinoline quinone (PQQ) 18%, wintergreen oil 0.6%, sodium nitrate 0.3%, and oxymetazoline hydrochloride 0.05%.

The composition can include a carrier medium, such as water.

In certain implementation, the disclosed composition can also include suitable preservatives, such as benzalkonium chloride.

In certain implementations, the disclosed composition can be prepared by mixing at least the ingredients including reduced glutathione (GSH), *Mentha* oil, pyrroloquinoline quinone (PQQ), wintergreen oil, sodium nitrate, and oxymetazoline hydrochloride. The disclosed composition can also include neutral excipients for the formulation, and any such neutral excipients are within the scope of the present invention. The disclosed composition can be administered through the nasal route. A suitable formulation for nasal administration, such as for the atomizers can be formulated from the disclosed composition. Similarly, the formulations for inhalers can be formulated using the disclosed composition. The excipients and processes for nasal formulations are known to a skilled person, and any such formulation for nasal administration and the process of formulating the composition for nasal administration are within the scope of the present invention.

In certain implementations, the dose for children and adults can be determined by suitable experimentation. Any such methods for determining the dose for children and adults are within the scope of the present invention.

In certain implementation, the excipients can include a range of functional excipients, such as solvents, solubilizers, surfactants, buffering agents; antioxidants; preservatives; osmolality agents; penetration enhancers; suspending agents, and the like. Examples of preservatives include benzalkonium chloride, benzyl alcohol, and parabens. Examples of surfactants include polysorbate-20 and polysorbate-80. Some common excipients that can be used include starch, lactose, crystalline cellulose, calcium lactate, magnesium aluminometasilicate, and anhydrous silicate.

In experimental results, it was found that the composition was active against viruses. For example, it was found that disclosed composition could kill influenza viruses in 20 seconds, wherein the kill rate was about 99.99%. Similar experiments were conducted on corona viruses and RSV viruses and the kill rate was found to be above 99%.

Also, it is to be noted that that the disclosed composition has been FDA approved for OTC without a prescription. FDA has approved the label for the disclosed composition.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

5 6

What is claimed is:

1. A formulation for treatment of respiratory diseases and providing relief in the symptoms of respiratory diseases, the formulation comprising:

a composition comprising, by volume percent thereof:

reduced glutathione 50-80.45%;

*Mentha* oil 0.2-4%;

pyrroloquinoline quinone 10-30%;

wintergreen oil 0.2-4%;

sodium nitrate 0.1-0.5%; and oxymetazoline hydrochloride 0.01-0.10%; and an amount of excipients.

2. A nasal dosage form for treatment and relief of respiratory diseases, the nasal dosage form comprising:

a composition comprising, by volume percent thereof:

reduced glutathione 50-80.45%;

*Mentha* oil 0.2-4%;

pyrroloquinoline quinone 10-30%;

wintergreen oil 0.2-4%;

sodium nitrate 0.1-0.5%; and oxymetazoline hydrochloride 0.01-0.10%; and an amount of excipients.

3. A method for treatment and providing relief in respiratory diseases, the method comprising the steps of:

providing a formulation comprising a composition and excipients, wherein the composition comprises reduced glutathione, *Mentha* oil, pyrroloquinoline quinone, wintergreen oil, sodium nitrate, and oxymetazoline hydrochloride; and administering the formulation composition through a nasal route, wherein, by volume percent of the composition, the reduced glutathione is present in an amount ranging from 50-89.49%; the *Mentha* oil is present in an amount ranging from 0.2-4%; the pyrroloquinoline quinone is present in an amount ranging from 10-30%; the wintergreen oil is present in an amount ranging from 0.2-4%; the sodium nitrate is present in an amount ranging from 0.1-0.5%; and the oxymetazoline hydrochloride is present in an amount ranging from 0.01-0.10%.

4. The method according to claim 3, wherein the respiratory diseases is a viral infection.

5. The method of claim 3, wherein the composition comprises reduced glutathione (GSH) 80.45%, *Mentha* oil 0.6%, pyrroloquinoline quinone (PQQ) 18%, wintergreen oil 0.6%, sodium nitrate 0.3%, and oxymetazoline hydrochloride 0.05%.

* * * * *